(12) United States Patent
Wait

(10) Patent No.: US 9,095,438 B1
(45) Date of Patent: Aug. 4, 2015

(54) SURGICAL IMPLANT FOR OSTECTOMY PROCEDURES

(71) Applicant: Ellen S. Wait, Hayden, ID (US)

(72) Inventor: Ellen S. Wait, Hayden, ID (US)

(*) Notice: Subject to any disclaimer, the term of this patent is extended or adjusted under 35 U.S.C. 154(b) by 0 days.

(21) Appl. No.: 14/108,011

(22) Filed: Dec. 16, 2013

Related U.S. Application Data

(60) Provisional application No. 61/797,798, filed on Dec. 17, 2012.

(51) Int. Cl.
*A61F 2/32* (2006.01)
*A61F 2/36* (2006.01)

(52) U.S. Cl.
CPC .................... *A61F 2/3609* (2013.01)

(58) Field of Classification Search
CPC ..... A61F 2/32; A61F 2220/0033; A61F 2/36; A61F 2/36; A61F 2/36091
USPC ....................... 623/22.15–22.19, 23.11–23.14
See application file for complete search history.

(56) References Cited

U.S. PATENT DOCUMENTS

| 6,110,211 A * | 8/2000 | Weiss ..................... 623/23.11 |
| 6,488,716 B1 | 12/2002 | Huang et al. |
| 7,211,113 B2 | 5/2007 | Zelener et al. |
| 7,931,691 B2 | 4/2011 | Li et al. |
| 8,029,573 B2 | 10/2011 | Podolsky |
| 2011/0202138 A1 | 8/2011 | Shenoy et al. |
| 2011/0213466 A1 | 9/2011 | Shenoy et al. |
| 2012/0130504 A1 | 5/2012 | Forsell |

FOREIGN PATENT DOCUMENTS

EP  2 452 641 A1  5/2012

* cited by examiner

*Primary Examiner* — Jason-Dennis Stewart
(74) *Attorney, Agent, or Firm* — Lee & Hayes, PLLC

(57) ABSTRACT

In one instance, the disclosure is a moldable, biocompatible, bioactive, and resorbable hip implant made to be implanted after femoral head ostectomy. The hip implant can be configured so that a portion of the implant can fit into the femoral canal after the femoral head is excised, and another portion can fit into the joint space. The hip implant can be configured to have a honeycomb structure capable of receiving and retaining materials such as antibiotics, stem cells, and platelet rich plasma for treatment after femoral head ostectomy. The resorbable material comprising the hip implant can degrade or dissolve over time and be resorbed by the body while scar tissue forms a pseudoarthrosis in place of the resorbed hip implant.

24 Claims, 5 Drawing Sheets

SURGICAL IMPLANT FOR OSTECTOMY PROCEDURES

CROSS REFERENCE TO RELATED APPLICATION

This application claims the benefit of U.S. Provisional Application No. 61/797,798, filed on Dec. 17, 2012, the disclosure of which is incorporated herein by reference in its entirety.

TECHNICAL FIELD

The present disclosure relates to surgical implants.

BACKGROUND

In the field of veterinary medicine, three primary treatments have been used for animals with chronic and degenerative hip conditions such as congenital dysplasia, Legg-Calve-Perthes disease, avascular necrosis, and recurrent dislocation. The first treatment method is conservative management, wherein medication, exercise, and nutrition are regulated in an attempt to decrease pain in the animal and increase range of motion. This treatment method, while minimally invasive and comparatively inexpensive, only slows the degeneration of the hip joint but does not cure the condition or stop its progression. Also, conservative management can typically only be used in mild or early cases of degenerative hip disease and thus does not afford a lasting solution to many animals.

The second treatment method is total hip replacement. This method includes excising the femoral head and neck and reshaping the acetabular surface. Metal prosthetic components are inserted into the joint, shaped to act as a replacement femoral head, neck, and acetabulum. This treatment method requires specialized veterinary care, is comparatively the most expensive treatment method, and can lead to surgical and long term complications, especially in larger animals. The cost-prohibitive nature of this treatment method and required technical expertise make it a viable solution in only certain circumstances.

The third treatment method is femoral head ostectomy. As with total hip replacement, the femoral head and neck are excised. However, unlike total hip replacement, no replacement femoral head or neck is used, and the joint space is left vacant following the femoral head ostectomy. The affected leg is unable to support weight-bearing for several weeks while fibrous scar tissue forms in the joint space, eventually forming a pseudoarthrosis or false joint. While this treatment method can permit some functional recovery of the joint and serviceable weight bearing, recovery time can span multiple weeks or months and postoperative rehabilitation can be six months or longer. Postoperative leg length discrepancy and gait abnormalities are common, especially in larger animals and larger breeds of smaller animals that historically have less predictable outcomes. While less costly than total hip replacement, femoral head ostectomy provides for only limited functional recovery of the joint, and the animal is at higher risk for complications while activity is compromised. In short, femoral head ostectomy has typically been considered a last-resort salvage operation with the primary purpose of relieving pain, not returning to early and full mobility.

SUMMARY OF THE DISCLOSURE

In accordance with embodiments of the present invention, a resorbable, bioactive, biocompatible, and moldable hip implant made to fit into the joint space following femoral head excision is provided.

In one embodiment, the present disclosure provides a hip implant having a proximal end formed to replicate a femoral head and fit into the joint space, and a distal end formed to replicate a femoral neck and fit into the femoral canal after femoral head ostectomy. The hip implant can comprise a substantially moldable material configured for a custom fit into the joint space and femoral canal of animals of differing sizes. The hip implant's moldable material can also be configured to receive sutures so as to allow a veterinarian to suture the hip implant to bone or soft issues in and around the joint.

In accordance with some embodiments, the present disclosure provides a hip implant made of a biocompatible and resorbable material. The biocompatible material can be configured such that the material, when implanted, will not be rejected as a foreign substance by the body. The resorbable material can be configured such that the material, when implanted into the body, will degrade or dissolve over time at the same or similar rate that scar tissue is forming, and can be resorbed by the body as it degrades. The by-products of the degraded or dissolved implant can be nontoxic. Scar tissue can assume and fill the space left by the resorbed hip implant.

In another embodiment, the present disclosure provides a hip implant comprising a temporary prosthetic femoral head and neck comprising a plurality of recesses or apertures. In some embodiments, the temporary femoral head and neck may comprise a honeycomb structure defining a plurality of cells extending across and through the temporary femoral head and neck. The cells may define a plurality of apertures having varying depths. The apertures on the surface of the prosthetic femoral head and neck may be used to accept infusion of a variety of therapeutic materials, such as antibiotics, stem cells, or platelet rich plasma gel. Infusion of such materials into the honeycomb-shaped prosthetic femoral head and neck can provide direct delivery of therapeutic substances to the affected joint, imparting a bioactive property.

In these and other embodiments, the present disclosure will become more readily appreciated and understood from a consideration of the following detailed description of the exemplary embodiments of the present disclosure when taken together with the accompanying drawings.

DETAILED DESCRIPTION

As can be seen in the embodiments shown in FIGS. 1-7, a surgical implant may comprise a biocompatible, bioactive, resorbable, and moldable hip implant configured to serve as a temporary three dimensional scaffolding in place of an excised femoral head and neck.

Figure 1:
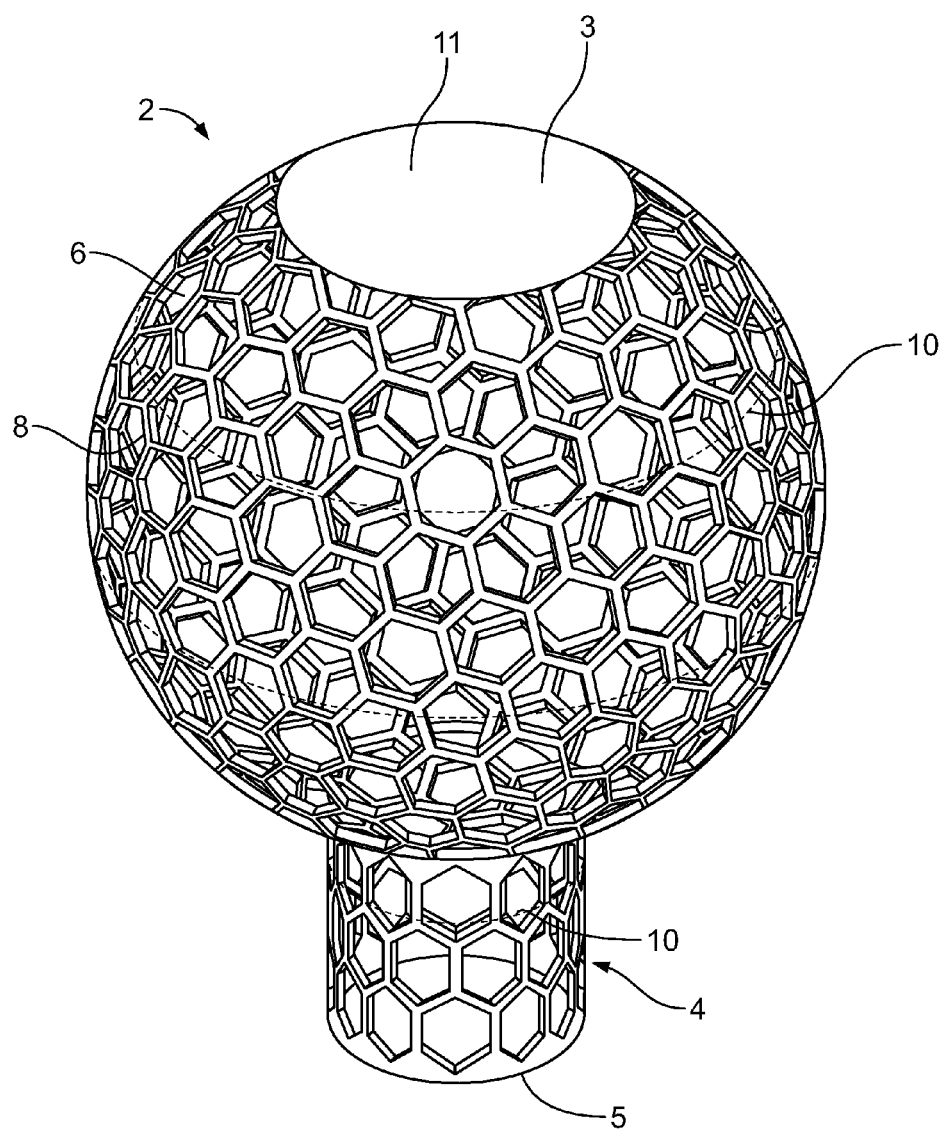
FIG. 1 shows a side view of a hip implant.
Figure 2:
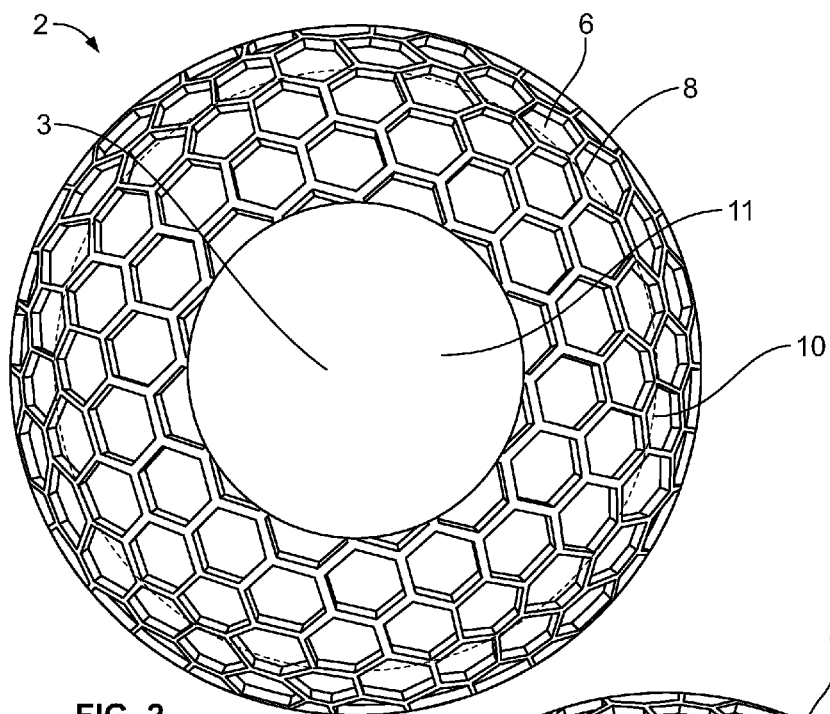
FIG. 2 shows a top view of a hip implant.
Figure 3:
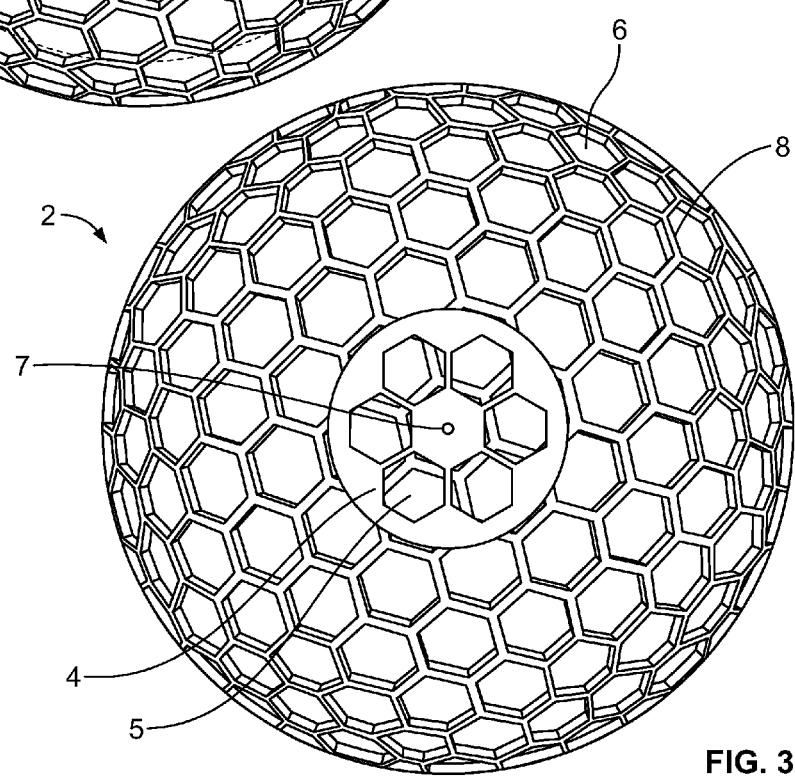
FIG. 3 shows a bottom view of a hip implant.

Referring to FIGS. 1-3, a side, top, and bottom view, respectively, of a hip implant in accordance with embodiments of the present invention is provided. The hip implant may comprise a first component 2 and a second component 4.

The first component 2 can be configured to replicate the shape of a femoral head and be received in the joint space after excision of the femoral head. The first component 2 is described herein as the "temporary femoral head." The second component 4 can be configured to replicate the shape of a femoral neck and can be further configured to fit into a femoral canal after excision of a femoral head and neck. The second component 4 is described herein as the "temporary femoral neck." The first component 2 and second component 4 can be a singular piece, or can be separate pieces combined by biocompatible adhesive. The hip implant can have a proximal end 3 and a distal end 5. The temporary femoral head 2 and the temporary femoral neck 4, when combined and implanted in the subject, can be positioned in the region within the hip where the subject's original femoral head and neck had been located. However, in contrast with traditional hip replacement implants, the temporary femoral head 2 and the temporary femoral neck 4 are not configured to provide a permanent replacement of the original femoral head and neck. Instead, the temporary femoral head 2 and the temporary femoral neck 4 provide a temporary scaffold. This temporary scaffold may provide sufficient structural support to afford increased stability of the joint and sustain early weight bearing, thereby minimizing leg length discrepancy following the ostectomy procedure while the fibrous scar tissue and pseudoarthrosis are formed in the joint space following excision of the femoral head and neck.

Figure 4:
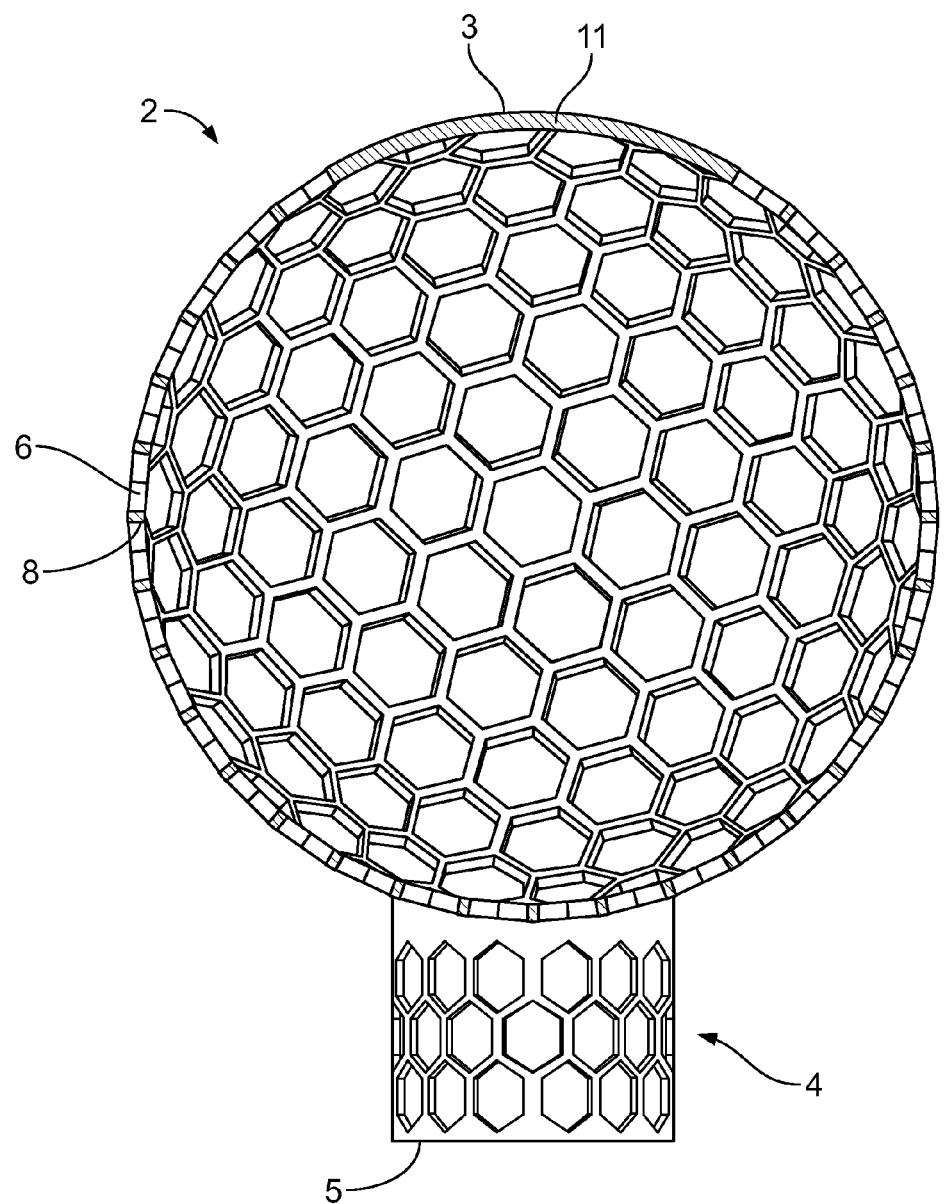
FIG. 4 shows a cross-sectional view of a hip implant as viewed from the side of the hip implant.

In accordance with embodiments of the present invention, the temporary femoral head 2 may have openings, slits, apertures, or recesses. Referring to FIGS. 1-3, the temporary femoral head 2 and the temporary femoral neck 4 can comprise a honeycomb structure 6 defining a plurality of cells extending across and through the temporary femoral head 2 and temporary femoral neck 4. The cells may define a plurality of apertures covering all or a portion of the exterior surface of the temporary femoral head 2 and temporary femoral neck 4. The cells of the honeycomb structure 6 can have any number of sides 8 and can be a variety of sizes. The cells of the honeycomb structure 6 can also have a uniform number of sides 8 and sizes, or the cells can vary in number of sides 8 and in sizes on the same temporary femoral head 2 or temporary femoral neck 4. By way of example, in one embodiment, the cells of the honeycomb structure 6 can be of uniform size, each having 6 sides 8 with side lengths of approximately 4 millimeters. The density of honeycombs in the honeycomb structure 6 can vary from the center of the hip implant to the exterior surface of the hip implant. In one embodiment, there can be a higher density of honeycombs (with each honeycomb having minimal depth and size) near the center of the hip implant, and a lower density of honeycombs (each honeycomb having increased depth and size) near the exterior surface of the hip implant. In another embodiment, as shown in FIG. 4, the density of honeycombs in the honeycomb structure 6 can be substantially uniform throughout the temporary femoral head 2 and temporary femoral neck 4. In one embodiment, shown in FIG. 1, the proximal end 3 of the temporary femoral head 2 can have a smooth surface 11. The smooth surface 11 can vary in surface area to cover all or a portion of the proximal end 3 of the temporary femoral head 2.

Referring to FIG. 3, the temporary femoral neck 4 can have a hole or port 7 on the distal end 5 of the hip implant. The port 7 can be the diameter of a syringe tip and can provide access to the interior of the temporary femoral neck 4 and temporary femoral head 2. The temporary femoral head 2 may also have a port 7.

Referring next to FIG. 4, a cross-sectional view of the hip implant is shown. The temporary femoral head 2 and temporary femoral neck 4 may comprise a honeycomb structure 6 as described above. The cells of the honeycomb structure 6 can have a depth as small as a fraction of a millimeter and as large as the radius of the temporary femoral head 2. Honeycomb cell depth can be uniform or can vary in any particular embodiment of the hip implant.

Figure 5:
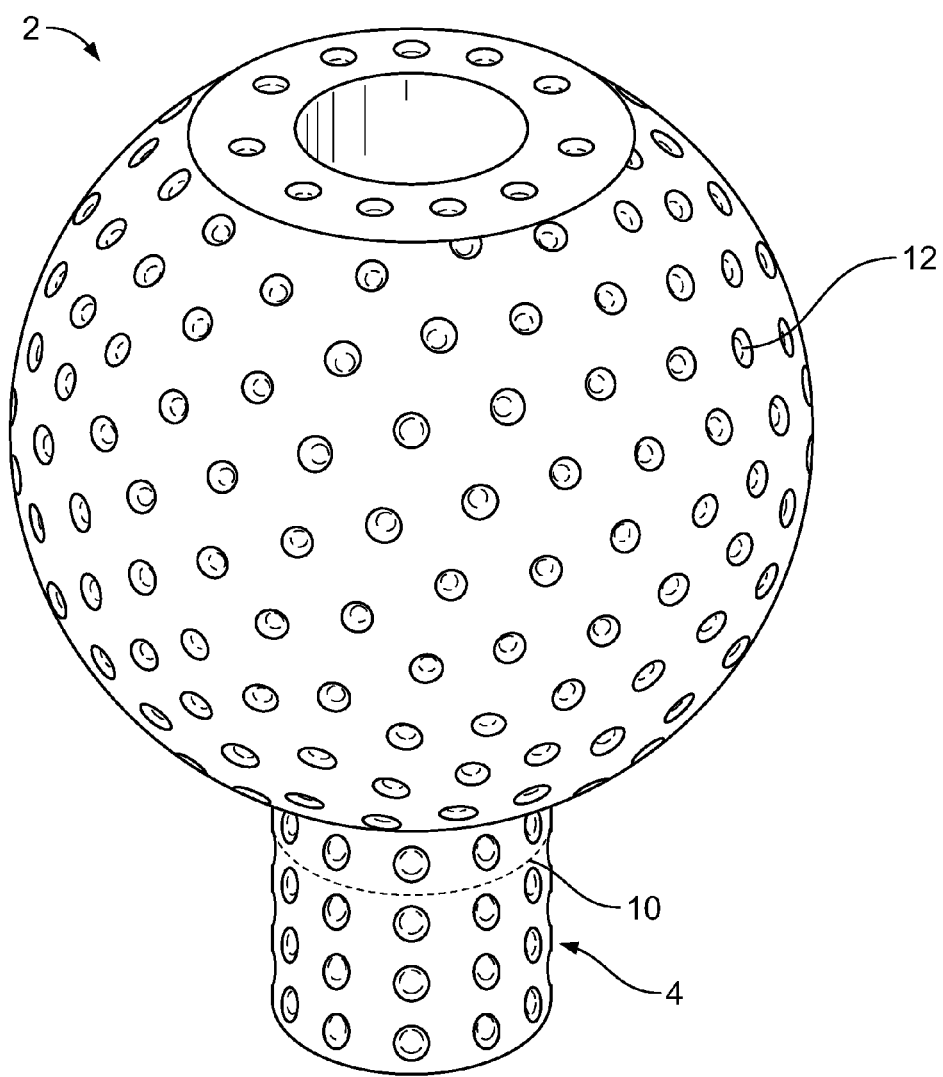
FIG. 5 shows a side view of a hip implant.

Referring next to FIG. 5, a side view of the hip implant is shown. The exterior of the temporary femoral head 2 can include a plurality of indents 12. The plurality of indents 12 can be any geometry, such as circular, square, or triangular. The plurality of indents 12 can also be shallow or can extend to the center of the temporary femoral head 2. Also as seen in FIG. 5, the proximal end 3 of the temporary femoral head 2 can be smooth and slightly rounded to provide nonabrasive contact with the acetabular interface. When the temporary femoral head 2 has at least a partially hollow interior, the proximal end 3 of the temporary femoral head 2 can have a hole, allowing access to the interior of the temporary femoral head 2.

The temporary femoral neck 4, can be straight or bent at an angle similar to an anatomical femoral neck. The bend in the temporary femoral neck 4 can be placed at any part of the temporary femoral neck 4, including where the temporary femoral head 2 and temporary femoral neck 4 meet.

The hip implant described herein can be made of a biocompatible material suitable for implantation into an animal subject. This biocompatible material may be selected so as to minimize rejection potential in the implanted subject. By way of example, biocompatible materials that can be used pursuant to the present disclosure include: acellular collagen membranes, gelatin, polysaccharides, and fibrin. As used in the art, biocompatible materials can also be known as biomaterials and can be used accordingly to the present disclosure. The biomaterials can be synthetic or natural materials, and can be a material suitable for biocompatibility when implanted adjacent to bone, cartilage, and muscle tissue.

The hip implant described herein can also be made of a resorbable material configured such that when implanted in the body, the material degrades or dissolves over time and is resorbed by the body. The time period for degradation or dissolution can depend on the material used and the size of the hip implant. By way of example, a resorbable material that can be used for the present disclosure is an acellular collagen membrane. As used in this disclosure, materials that dissolve in the body over time can do so such that the hip implant is a soluble material and acts as a solute in the body. The body's natural chemistry, including blood and lymphatic and synovial fluids, can act as a solvent, and the body's temperature, pressure, and pH levels can promote the dissolution of the hip implant at varying rates. As dissolution of the hip implant occurs, the crystalline structure of the hip implant can be dissolved into varying ions and molecules that are soluble in blood. When the hip implant is implanted into a larger animal, the hip implant can be larger than a hip implant fitted for a smaller animal. Accordingly, the larger hip implant may take more time than the smaller hip implant to degrade completely.

The hip implant described herein can also be made of a moldable material configured to allow the temporary femoral head 2, the temporary femoral neck 4, or both to be molded to fit varying sizes and shapes of joint spaces and femoral canals. By way of example, the hip implant can be made of a moldable material such as an acellular collagen membrane. The moldable material can be a polymer of sufficient crystallinity to maintain its formed shape and provide a certain level of structural support, but also having a low enough rigidity to allow the material to flex when force is applied. In one embodiment, the moldable material can be comprised of a mixture of crystalline and amorphous regions. The crystalline portion of the moldable material may be porous, allowing amorphous materials to pass through the pores of the material. Naturally occurring materials, such as collagen, gelatin, polysaccharides, and fibrin may be use in the present disclosure. Synthetic materials may also be used, such as poly(a-hydroxy esters), poly(e-caprolactone), poly(orthoesters), poly(anhydrides), PEG-based materials, poly(amino acids), fumarate-based materials, and poly-96L/4D-lactide copolymers.

Referring back to FIG. 1, in one embodiment, the temporary femoral head 2, temporary femoral neck 4, or both can comprise a material suitable to permit a needle or other sewing device to penetrate the exterior of the hip implant. In this embodiment, the hip implant can be secured to the femur and surrounding bodily tissue by suturing the hip implant directly into that anatomy. One having ordinary skill in the art will be familiar with suturing implants into varying types of tissue.

In another embodiment, as shown in FIGS. 1, 2, and 5, the temporary femoral head 2, temporary femoral neck 4, or both can include suturing holes 10 or other anchoring features configured to allow a needle to pass into and out of the holes 10 for the purpose of suturing the hip implant to the femur and surrounding tissue. One having ordinary skill in the art will be familiar with suturing implants into varying types of tissue.

The hip implant described herein can be configured so that the cells of the honeycomb structure 6 on the temporary femoral head 2 and temporary femoral neck 4 can receive and retain therapeutic materials. By way of example, a veterinarian may choose to place antibiotics, stem cells, or platelet rich plasma gel into one or many of the cells in the honeycomb structure 6 of the hip implant. Antibiotic placement in the honeycomb structure 6 can provide targeted antibiotic treatment to the joint once the hip implant is placed. Such antibiotic treatment can decrease the risk of infection and harmful results of the same. Stem cell placement in the honeycomb structure 6 can promote the growth of cartilage at the joint surface, bone growth from the femur, and scar tissue in the joint space as the hip implant is resorbed by the body. Platelet rich plasma placement can promote healing and scar tissue growth, which can lead to decreased recovery time.

In one embodiment, the presently disclosed hip implant can be made using any method of polymeric molding. By way of example, the hip implant can be made by creating an injection mold of the hip implant and injecting a biocompatible, resorbable, and moldable polymer or polymeric mixture into the mold. One having ordinary skill in the art will know the temperature, pressure, and time required to create a molded hip implant by the injection molding technique described herein. When making the presently disclosed hip implant, the implant can be made so that its interior is at least partially hollow or the interior can be completely filled with biocompatible, resorbable, and moldable material. The honeycomb structure 6 can also be made to make up only the exterior of the hip implant, or can extend into the interior of the hip implant. When determining the size of the hip implant needed in a given application, animal size by body weight and anatomical measure, such as through pre-operative radiograph can be considered. In one embodiment wherein the material making up the hip implant is porous, surfactants can be used in the polymeric mixture to create micelles having a hydrophilic exterior and hydrophobic interior. The polymeric mixture can then form around the micelles when mixed with the surfactant, which can be burned or otherwise heated away during the injection molding process.

In another embodiment, the presently disclosed hip implant can be made using three-dimensional printing. By way of example, three-dimensional printing can be accomplished by creating scaffolding customized to computed tomography scanning that resembles the femoral head and neck. The scaffolding can then be coated with stem cells, which can develop into different tissue types. The scaffolding can then be coated with a polymer, such as polylactic acid, and a gel, such as alginate, to promote a hardened exterior.

Figure 6:
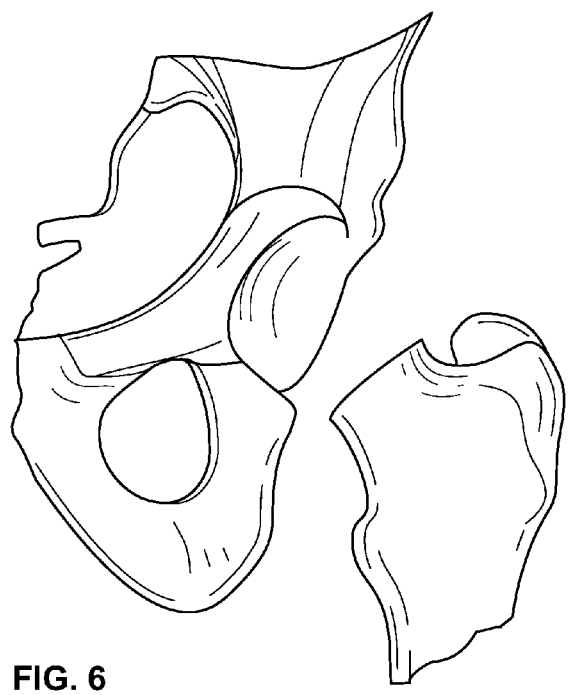
FIG. 6 shows an illustration of an acetabulum and femur after femoral head and neck excision.

In use, a veterinarian or someone skilled in veterinary surgery can first perform a femoral head ostectomy as would be performed without the use of the hip implant. By way of example, the patient can be anesthetized and then placed in lateral recumbency with the affected limb hung and aseptically prepared for surgery. A skin incision can then be made, revealing the musculature of the affected limb. The plane between the tensor fascia lata and biceps femoris can then be incised and separated, and the tensor fascia and biceps musculature can be retracted. The superficial and middle gluteal muscles can then be retracted without excision of the musculature or tendinous insertions. Elevation of the deep gluteal muscle tendon can allow identification of the underlying hip joint capsule. The hip joint capsule can then be incised along the acetabulum and onto the femoral neck. The femoral head can then be freed from the acetabulum joint and excised. The remaining femur and acetabular bone can be smoothed to ensure no grinding occurs. FIG. 6 represents an illustration of a completed femoral head ostectomy.

Figure 7:
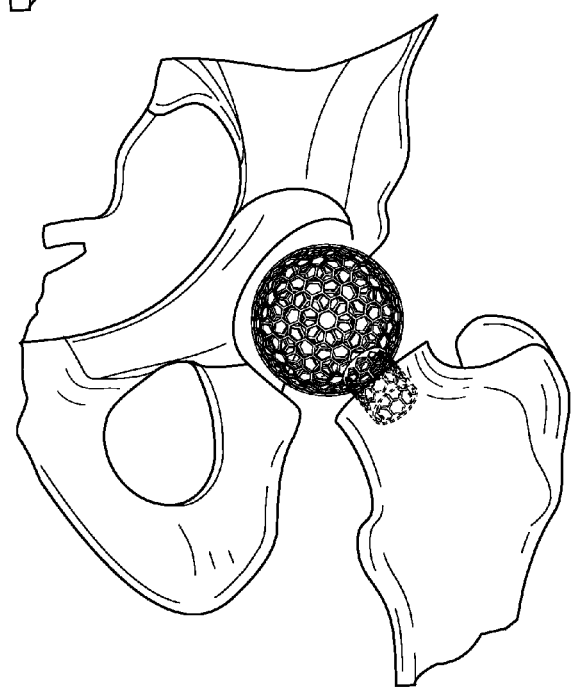
FIG. 7 shows an illustration of a hip implant when implanted.

After excision of the femoral head and neck, the surgeon can place the temporary femoral neck 4 into the femoral canal, which is exposed after excision, as shown in FIG. 7. Either during or before the surgery, the surgeon or other veterinarian can place materials such as antibiotics, stem cells, platelet rich plasma, or other medication into the honeycomb structure 6 that makes up at least a portion of the temporary femoral head 2 and temporary femoral neck 4. If desired, the surgeon can mold the temporary femoral neck 4 by squeezing or otherwise applying pressure thereto until the temporary femoral neck 4 is sized to fit the femoral canal. The surgeon can then attach the temporary femoral neck 4 to the femur, such as by sutures. The surgeon can then fit the temporary femoral head 2 into the joint space, as shown in FIG. 7. If desired, the surgeon can mold the temporary femoral head 2 by squeezing or otherwise applying pressure thereto until the temporary femoral head 2 is sized to fit into the joint space. The surgeon can then attach the temporary femoral head 2 to surrounding bodily tissue, such as by sutures. One having ordinary skill in the art could then complete the surgery as would be typically done in a total hip replacement procedure. By way of example, the surgical area can be flushed with sterile saline, and the surgical site can be closed by closing any residual joint capsule over the acetabulum using absorbable sutures. Affected tendons can be reattached to the deep tissue of the joint by interrupted sutures. All other tissues can be closed using sutures.

In the initial stage of recovery, the hip implant may allow the patient to bear weight immediately on the affected hip, which can facilitate the formation of fibrous tissue, reduce pain, preserve muscle strength, and provide the patient the ability to resume activity. Throughout recovery, as described above, the hip implant can degrade or dissolve over time as fibrous tissue forms where the femoral head once was. The hip implant can be resorbed by the body until it is eliminated and a pseudoarthrosis exists in its place.

It is to be understood that while the present disclosure describes one embodiment of a hip implant for use in veterinary medicine, the hip implant described herein can be made and implanted into human patients suffering from congenital hip conditions, severe trauma, sepsis, recurrent dislocation, or failure of previous reconstruction. Use of the presently described implant may also find application in joints other than the hip joint.

Exemplary Embodiments

The following paragraphs represent the many embodiments of the present disclosure but this section is not an exclusive description of all embodiments of the present disclosure.

1. A hip implant for implantation into a subject, comprising a body comprised of a head portion and a neck portion, the head portion sized to be received in a joint space, the neck portion coupled to the head portion and configured to fit inside a femoral canal, and wherein the head portion and the neck portion comprise resorbable materials.
2. The device of paragraph 1, wherein the head portion is substantially spherical.
3. The device of any and all of paragraphs 1-2, wherein the neck portion is substantially cylindrical.
4. The device of any and all of paragraphs 1-3, wherein the body comprises a material capable of being molded when force is applied to the body.
5. The device of any and all of paragraphs 1-4, wherein the body comprises a biocompatible material.
6. The device of any and all of paragraphs 1-5, wherein the body comprises a plurality of recesses on its exterior.
7. The device of any and all of paragraphs 1-6, wherein the head portion and the neck portion comprise a honeycomb structure defining a plurality of cells.
8. The device of any and all of paragraphs 1-7, wherein each honeycomb in the honeycomb structure has at least three sides.
9. The device of any and all of paragraphs 1-8, further comprising a therapeutic substance contained in at least some of the plurality of cells.
10. The device of any and all of paragraphs 1-9, wherein the therapeutic substance comprises an antibiotic.
11. The device of any and all of paragraphs 1-10, wherein the therapeutic substance comprises a platelet rich plasma.
12. The device of any and all of paragraphs 1-11, wherein the therapeutic substance comprises stem cells.
13. The device of any and all of paragraphs 1-12, wherein the body further includes one or more holes configured to accept a needle for suturing.
14. A hip implant for implantation into a subject, comprising a body having two components, the first component configured to be substantially spherical, and the second component configured to be substantially cylindrical, the first component further configured to fit into a joint space, the second component further configured to fit into a femoral canal, the first component lockedly engaged to the second component, and the first component and second component comprise a resorbable material.
15. The device of paragraph 14, wherein the first component and second component comprise a biocompatible material.
16. The device of any and all of paragraphs 14-15, wherein the first component and second component comprise a material capable of being molded when force is applied to the body.
17. The device of any and all of paragraphs 14-16, wherein an exterior surface of the first component and second component comprises a plurality of recesses.
18. The device of any and all of paragraphs 14-17, wherein the first component and the second component comprise a honeycomb structure defining a plurality of cells.
19. The device of any and all of paragraphs 14-18, wherein each honeycomb in the honeycomb structure has at least three sides.
20. The device of any and all of paragraphs 14-19, further comprising a therapeutic substance contained in at least some of the plurality of cells.
21. The device of any and all of paragraphs 14-20, wherein the therapeutic substance comprises an antibiotic.
22. The device of any and all of paragraphs 14-21, wherein the therapeutic substance comprises a platelet rich plasma.
23. The device of any and all of paragraphs 14-22, wherein the therapeutic substance comprises stem cells.
24. The device of any and all of paragraphs 14-23, wherein the first component and the second component further includes one or more holes configured to accept a needle for suturing.

The elements and limitations described in Paragraphs 1-24 can be combined with each other to create a surgical hip implant.

While certain embodiments of the present disclosure have been disclosed in detail, it is to be understood that various modifications may be adopted without departing from the spirit of the disclosure.

Unless otherwise indicated, all numbers expressing quantities of ingredients used in the specification and claims are to be understood as being modified in all instances by the term "about." Accordingly, unless indicated to the contrary, the numerical parameters set forth in the specification and attached claims and embodiments are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventor for carrying out the invention. Of course, variations on these described embodiments will become apparent to those of ordinary skill in the art upon reading the foregoing description. The inventor expects skilled artisans to employ such variations as appropriate, and the inventor intends for the invention to be practiced otherwise than specifically described herein. Accordingly, this invention includes all modifications and equivalents of the subject matter recited in the claims appended hereto as permitted by applicable law. Moreover, any combination of the above described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

What is claimed is:

1. A hip implant for implantation into a subject, comprising:
   a body comprised of a head portion and a neck portion;
   the head portion sized to be received in a joint space; the neck portion coupled to the head portion and configured to fit inside a femoral canal;
   the head portion comprising a spherically-shaped solid mass made from a porous material; and
   wherein the head portion and the neck portion comprise resorbable materials.
2. The device of claim 1, wherein:
   the head portion is substantially spherical.
3. The device of claim 1, wherein:
   the neck portion is substantially cylindrical.
4. The device of claim 1, wherein:
   the body comprises a material capable of being molded when force is applied to the body.
5. The device of claim 1, wherein:
   the body comprises a biocompatible material.
6. The device of claim 1, wherein:
   the body comprises a plurality of recesses on its exterior.
7. The device of claim 1, wherein:
   the head portion and the neck portion comprise a honeycomb structure defining a plurality of cells.
8. The device of claim 7, wherein:
   each honeycomb in the honeycomb structure has at least three sides.
9. The device of claim 7, further comprising:
   a therapeutic substance contained in at least some of the plurality of cells.
10. The device of claim 9, wherein:
    the therapeutic substance comprises an antibiotic.
11. The device of claim 9, wherein:
    the therapeutic substance comprises a platelet rich plasma.
12. The device of claim 9, wherein:
    the therapeutic substance comprises stem cells.
13. The device of claim 1, wherein:
    the body further includes one or more holes configured to accept a needle for suturing.
14. A hip implant for implantation into a subject, comprising: a body having two components, wherein the first component is a substantially spherical solid mass made of a porous material, and the second component is substantially cylindrical;
    the first component further configured to fit into a joint space;
    the second component further configured to fit into a femoral canal;
    the first component lockedly engaged to the second component; and
    the first component and second component comprise a resorbable material.
15. The device of claim 14, wherein:
    the first component and second component comprise a biocompatible material.
16. The device of claim 14, wherein:
    the first component and second component comprise a material capable of being molded when force is applied to the body.
17. The device of claim 14, wherein:
    an exterior surface of the first component comprises a plurality of recesses.
18. The device of claim 14, wherein:
    the first component and the second component comprise a honeycomb structure defining a plurality of cells.
19. The device of claim 18, wherein:
    each honeycomb in the honeycomb structure has at least three sides.
20. The device of claim 18, further comprising:
    a therapeutic substance contained in at least some of the plurality of cells.
21. The device of claim 20, wherein:
    the therapeutic substance comprises an antibiotic.
22. The device of claim 20, wherein:
    the therapeutic substance comprises a platelet rich plasma.
23. The device of claim 20, wherein:
    the therapeutic substance comprises stem cells.
24. The device of claim 14, wherein:
    the first component and the second component further include one or more holes configured to accept a needle for suturing.

* * * * *